United States Patent [19]
LaPointe et al.

[11] 3,936,354
[45] Feb. 3, 1976

[54] ANTI-TUMOUR PRODUCT OF BACTERIAL ORIGIN

[76] Inventors: Jean-Rock LaPointe, 410 62nd Ave., Chomedey Laval, Quebec; Victorien Fredette, 331 Tait, Ville St. Laurent, Quebec, both of Canada

[22] Filed: Apr. 29, 1974

[21] Appl. No.: 465,074

[52] U.S. Cl. .................................. 195/79; 195/100

[51] Int. Cl.$^2$ ........................ C12K 3/00; C12K 1/10

[58] Field of Search .......... 195/79, 96, 99, 102, 1.4, 195/DIG. 2, 112

[56] References Cited

UNITED STATES PATENTS 2,787,576 4/1957 Kakavas et al. ........................ 195/79

*Primary Examiner*—A. Louis Monacell
*Assistant Examiner*—C. A. Fan

[57] ABSTRACT

Wild strain Lechien of the organism Clostridium perfringens is attenuated with nitrosoguanidine. To produce an anti-tumor preparation, the attenuated organism is grown first on a growth medium then on a sporulation medium and the resulting growth recovered as a bacillary suspension, a spore suspension, or culture filtrates. The preparation in any of these forms has the property of inhibiting the growth of Ehrlich's solid tumor, of reducing the tumor size, and lengthening the survival time of the host.

3 Claims, No Drawings

ANTI-TUMOUR PRODUCT OF BACTERIAL ORIGIN

BACKGROUND OF THE INVENTION

1. Field of the Invention

This invention relates to a new attenuated strain of bacteria, an anti-tumor product, and a method for their preparation.

2. Description of the Prior Art

The wild strain Lechien of *Clostridium perfringens* (*Welchia perfringens*) is on deposit at the Institut Pasteur, Paris, France. This wild strain has pathogenicity for mice and guinea pigs.

SUMMARY OF THE INVENTION

The applicants have now developed a new attenuated strain of *Clostridium perfringens*, which they identify as LNG-11. This is derived by attenuating the wild Lechien strain with nitrosoguanidine. The new attenuated strain retains the original fermentation characteristics of the wild strain, but unlike the wild strain lacks pathogenicity for mice and guinea pigs.

To produce the anti-tumor product, the attenuated strain is grown by a sequential method first on a growth medium then on a sporulation medium in a cellophane tube apparatus as described by Vinet and Fredette in Science, Volume 114, No. 2969, pgs. 549–550, Nov. 23, 1951.

The growth medium may be Trypticase-Soy broth or other suitable growth medium. The sporulation medium is of the Wagenaar-Dack broth type. Growth is preferably carried out to substantially the maximum vegetative cell count. Sporulation is preferably carried out to substantially the maximum spore count. The resulting product is harvested as a bacillary suspension, a spore suspension or as filtrates. The activity of each is determined by intravenous injection in mice bearing Ehrlich's solid tumor.

The activity of the product is specific to tumor tissue and, at the same time lacks pathogenicity. The bacillary suspension, the spore suspension of filtrates, when injected into mice bearing Ehrlich's solid tumors have the property of reducing the tumor size, lengthening the survival of the mice, and, in a certain number of cases, bringing about complete regression of the tumors.

The following examples illustrate preferred procedures according to the invention.

EXAMPLE I

A fully virulent classical strain of *Clostridium perfringens* which is on deposit at the Institut Pasteur, Paris, France, was treated during its logarithmic growth phase with 100 $\mu$g/ml of N-methyl-N'-nitro-N-nitrosoguanidine, the bacteria being exposed to the mutagen for 30 minutes at 37°C in a phosphate buffer adjusted to pH = 6.2. After treatment the suspension was streaked on sheep blood agar plates and colonies which showed an alteration in the $\theta$-hemolysis pattern were selected for isolation. The resulting attenuated strain identified as LNG-11 was completely avirulent.

EXAMPLE II

The attenuated strain LNG-11 as prepared in Example I was grown at 37°C on Trypticase-Soy broth (Baltimore Biological Laboratories) for 48 hours. Then the medium was changed for modified version of Wagenaar and Dack's sporulation medium. Then the growth was carried on for an additional 48 hours. The growth was then harvested with centrifugation and washing. The supernatent was filtered on a 0.45 micron "Millipore" (trade mark) membrane.

EXAMPLE III

Ehrlich's solid carcinoma was maintained in male Swiss albino mice, weighing from 17 to 22 grams, by six weekly transfers in the peritoneal cavity. The mice were inoculated by the sub-continuous route using 0.5 millilitres of the fluid from the peritoneal cavity after 8 to 11 days, animals bearing a developed nodule were randomized for treatment with preparations from strain LNG-11. The product of Example II in the form of a bacillary suspension, a spore suspension, or filtrates was injected by the intravenous route, never using more than 0.5 millilitres per dose. When multiple doses had to be administered these were done at 24 hour intervals.

In mice bearing a 200 square millimeter tumor $100 \times 10^6$ vegetative cells produced a statistically significant retardation of tumor growth as did 10 doses of the corresponding crude filtrate. In large as well as in small tumors $4 \times 10^5$ to $4 \times 10^6$ viable thermoresistant spores induced a highly significant inhibition of tumor growth. The spores brought about an increase of at least 10 days in the mean survival time.

We claim:

1. A process of deriving an attenuated mutant strain of *Clostridium perfringens* which comprises attenuating the wild strain Lechien of *Clostridium perfringens* with N-methyl-N'-nitro-N-nitrosoguanidine.

2. A process of making an anti-tumor product effective against Ehrlich's solid tumor which comprises selecting an attenuated strain of *Clostridium perfringens* derived by attenuating the wild strain Lechien of *Clostridium perfringens* with N-methyl-N'-nitro-N-nitrosoguanidine growing the attenuated mutant strain by a sequential method using first a growth medium then on a sporulation medium in a cellophane tube apparatus, and recovering the resultant growth in the form of a bacillary suspension, a spore suspension or culture filtrates.

3. A composition comprising a liquid carrier and an antitumor product having specific activity to tumor tissue made by selecting the attenuated strain of *Clostridium perfringens* derived by attenuating the wild strain Lechien of *Clostridium perfringens* with N-methyl-N'-nitro-N-nitrosoquanidine, growing the attenuated strain by a sequential method first on a growth medium then on a sporulation medium in a cellophane tube apparatus, and recovering the attenuated strain in the form of a bacillary suspension, a spore suspension or culture filtrates, the product having the property of inhibiting the growth of Ehrlich's solid tumor, reducing the tumor size, and lengthening the survival time of the mice.

* * * * *